United States Patent [19]

Pevsner

[11] E Re. 31,272

[45] Reissued Jun. 14, 1983

[54] CATHETER DELIVERY SYSTEM AND METHOD

[76] Inventor: Paul H. Pevsner, 4121 King Crest Pkwy., Richmond, Va. 23221

[21] Appl. No.: 108,937

[22] Filed: Dec. 31, 1979

Related U.S. Patent Documents

Reissue of:

[64] Patent No.: 4,159,022
Issued: Jun. 26, 1979
Appl. No.: 790,622
Filed: Apr. 25, 1977

[51] Int. Cl.[3] ..... A61M 5/00

[52] U.S. Cl. ..... 604/28; 604/53; 604/159

[58] Field of Search ..... 128/214.4, 348-350, 128/DIG. 9, 274

[56] References Cited

U.S. PATENT DOCUMENTS 3,416,531 12/1968 Edwards ..... 128/348
3,703,174 11/1972 Smith ..... 128/214.4
3,859,985 1/1975 Eckhart ..... 128/274 X

FOREIGN PATENT DOCUMENTS 2415196 10/1975 Fed. Rep. of Germany ... 128/214.4

OTHER PUBLICATIONS

Pevsner-Amer. Jo. Roentgenol., vol. 128, Feb. 77, pp. 225-230.
Giesy-Jo. Am. A. Nurse Anest., Jun. 1972, pp. 181-184.
Cope-Circulation, vol. XXVII, Apr. 1963, pp. 758-761.
Cope-Jo. Applied Physiol., vol. 16, #5, Sep. 1961, pp. 917-918.
CSI Tech. Data Sheet-No. 215, Becton-Dickinson Inc., Nov. 1964.
CSI Tech. Data Sheet-No. 209-Becton-Dickinson Inc., Jan. 1967.
Cope-Jour. Thorac. Surgery-vol. 37, No. 4, Apr. 1959-pp. 482-486.

*Primary Examiner*—Dalton L. Truluck
*Attorney, Agent, or Firm*—Griffin, Branigan & Butler

[57] ABSTRACT

A catheter delivery system for delivering an elongated cannula-type catheter, normally including a cannula with an attachment on the tip thereof, to a body of a mammal and for controlling the movement of the cannula in the mammal's body includes both a cannula-control fitting and an enlarged hollow cannula delivery housing. The cannula control fitting has at least three openings therein. A cannula to be delivered to the mammal's body extends through the first and second openings of the cannula-control fitting and pressurized fluid can be inserted into the third opening. A sealing clamp is at the first opening for selectively, sealingly clamping the cannula-control fitting to the cannula. Thus, when the sealing clamp is tightened, fluid introduced at the third opening leaves the cannula-control fitting at the second opening. The hollow cannula delivery housing is attached to the third opening and has a relatively large cavity for receiving gathered portions of the cannula therein. The cannula delivery housing is attached to the third outlet of the cannula-control fitting at an inlet thereof and is attached to a mammal's blood vessel at an outlet thereof. The method of use is that the sealing clamp is tightened and the cannula is gathered in the cannula delivery housing. Pressurized fluid is introduced into the cannula-control fitting to drive the gathered cannula and its attachment from the cannula delivery housing into the mammal's blood vessel. Once all of the gathered cannula has been delivered to the mammal's body the sealing clamp is released and the proximal end of the cannula is controlled manually.

18 Claims, 4 Drawing Figures

CATHETER DELIVERY SYSTEM AND METHOD

Matter enclosed in heavy brackets [ ] appears in the original patent but forms no part of this reissue specification; matter printed in italics indicates the additions made by reissue.

BACKGROUND OF THE INVENTION

This invention relates broadly to the art of intravenous catheters, and more specifically to such catheters including long cannulas for carrying out surgical functions in remote parts of mammal bodies.

This application describes an advantageous method and apparatus, for example, for delivering the miniature balloon catheters described in U.S. patent application Ser. No. 681,676 of Paul H. Pevsner.

This invention also relates to U.S. Pat. Nos. 3,703,174 and 3,826,256 to Smith.

Basically, a procedure for using miniature intravenous balloon catheters in remote parts of the body involves firstly getting the catheter through a main artery of choice and secondly, guiding the catheter on a tortuous route to an exact blood vessel to be treated, such as in the brain, for example.

With regard to getting the catheter through the main artery, this can be done by first selectively catheterizing an artery of choice, such as the axillary, femoral, or common carotid artery using the Seldinger technique. In this respect, for example, a number five French polyethelyne catheter, or catheterizing tube, 11 (FIG. 1) can be inserted in the artery to extend from outside the patient's body to the approximate area to be treated. In this regard, it is not unusual for this tube to extend from below a patient's waist to above the patient's neck, for example. Next a balloon catheter, including a long cannula 13, can be pushed through this catheterizing tube 11 by a fluid under pressure.

In the past, feeding the cannula 13 through the catheterizing tube has been unduly cumbersome and messy because it has often been necessary to aid the feeding by manual manipulation of the proximal end of the cannula, which has allowed the pressurized propelling fluid to escape. Therefore, it is an object of this invention to provide a catheter delivery system which allows selective manual control of the proximal end of the cannula, where necessary, but yet which allows positive feeding of the cannula into a blood vessel by a pressurized fluid without significant leakage and without the necessity of manual feeding where allowed.

Once the tip of the cannula 13 passes beyond the distal end of the catheterizing tube 11, it must often be guided and manipulated through a tortuous system of blood vessels. To accomplish this, the balloon at the tip of the cannula 13 is successively inflated and deflated through the cannula 13 to be driven by blood flow to a greater or lesser degree as desired. During this portion of the procedure, it is essential that the doctor have manual control of the proximal end of the cannula.

Thus, it is an object of this invention to provide a catheter delivery system which not only allows positive driving of a cannula by fluid under pressure where allowed, but which also allows a doctor to have direct manual control of the cannula when either it is or is not being driven by a supplied propelling fluid.

It is a further object of this invention to provide a catheter delivery system which provides the above-mentioned advantages, but yet which is relatively uncomplicated to manufacture.

SUMMARY OF THE INVENTION

According to principles of this invention, an enlarged hollow cannula delivery housing is combined with a proximal flushing hub, or a cannula-control fitting. The cannula delivery housing has a relatively large cavity in which a gathered portion of the cannula can be stored for delivering the cannula through a catheterized artery. The cannula-control fitting allows positive fluid pressure to be applied to the cannula via the cannula delivery housing without leakage of the fluid, but yet also selectively allows the cannula to be manually gripped and manipulated when desired.

BRIEF DESCRIPTION OF THE DRAWINGS

The foregoing and other objects, features, and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION

Figure 1:
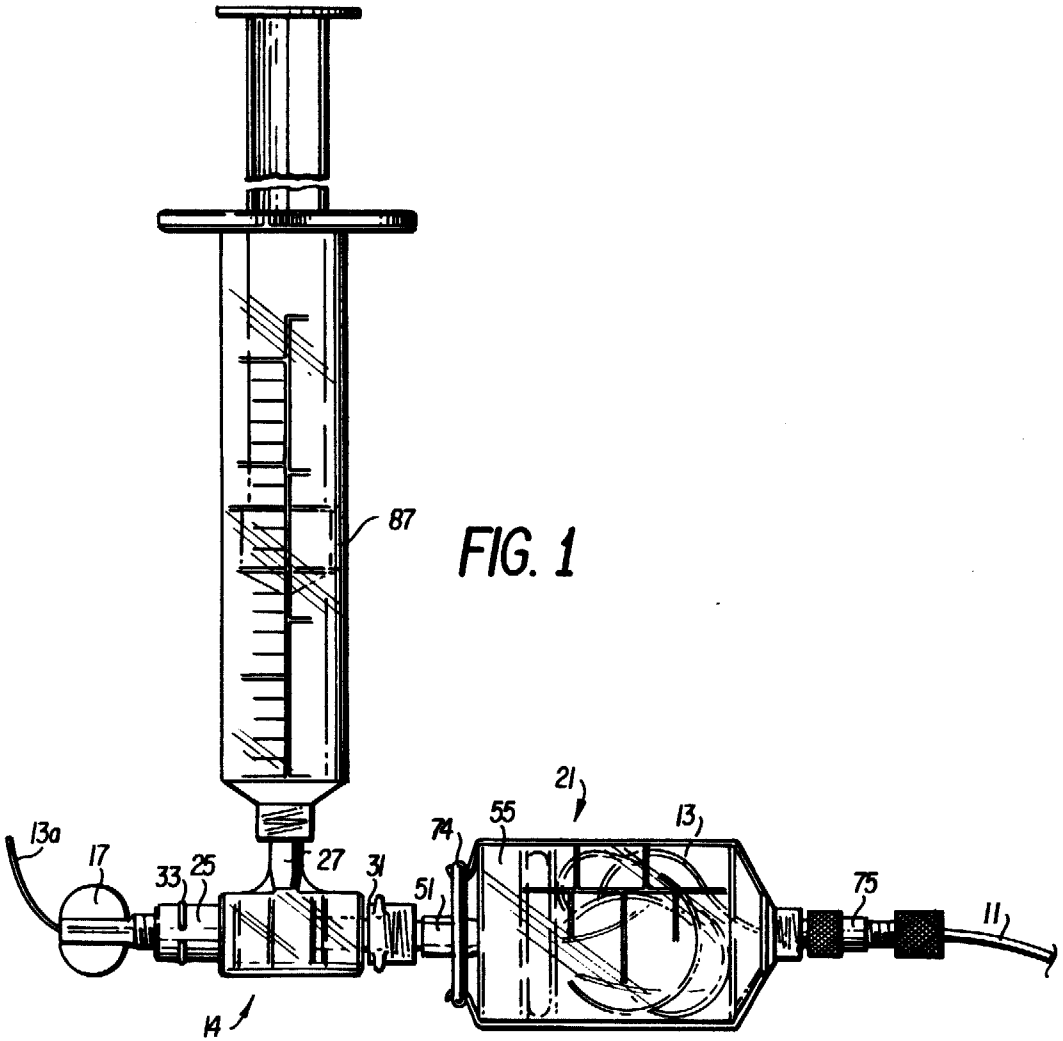
FIG. 1 is a side elevational view of a catheter delivery system employing principles of this invention, including a syringe, a catheterizing tube, and a catheter cannula.

A catheter delivery system of this invention includes a proximal flushing hub or cannula-control fitting 14, in combination with a hollow cannula delivery housing 21.

The cannula-control fitting 14, in the illustrated embodiment, is a spool valve basically comprising a sleeve 23 and a hollow spool 25 (such a device is sold by Becton-Dickinson as a guide-wire and catheter guide). The sleeve 23 forms a coupling member 27 having a passage 15 therethrough leading into the interior of the sleeve 23. The sleeve 23 makes sliding, sealing contact with O-rings 29 mounted in grooves of the spool 25. A shoulder 31 on the spool 25 and a metal C-ring 33 mounted in a groove on the spool 25 form stops for the sleeve 23 at limits of its motion along the spool. When the sleeve 23 is against the shoulder 31 in the position depicted in FIG. 2, the opening 15 communicates with the interior 35 of the spool 25 via a passageway 37 in the spool 25. On the other hand, when the sleeve 23 is against the C-ring 33, the opening 15 does not communicate with the interior 35 of the spool 25 but rather is cut off therefrom by the O-rings 29.

At its left end, (as viewed in FIGS. 1 and 4) the spool 25 has internal threads 39 which engage external threads 41 of a wing screw 17. When the wing screw 17 is tightened into the threads 39 a resilient washer 43 is squeezed between two rigid plastic washers 45 to form a seal between the interior wall of the spool 25 and the external wall of a cannula 13 positioned in the interior 35 of the spool 25. However, when the wing screw 17 is loose in the internal threads 39, an internal bore 47 of the resilient washer 43 allows the cannula 13 to move easily therethrough.

The right end of the spool 25 (as viewed in FIGS. 1 and 4) includes a mounting hub 49 for attaching the spool 25 to an adaptor 51 of the cannula delivery housing 21.

Figure 3:
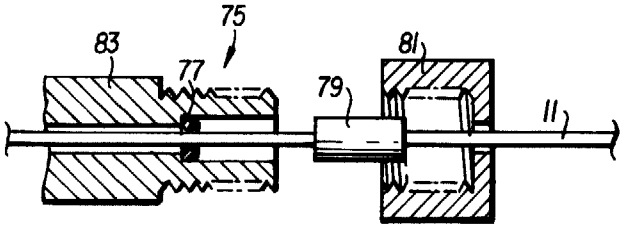
FIG. 3 is a sectional exploded view of an adaptor of the catheter delivery system of FIG. 1; and, FIG. 4 is an exploded, partially sectional, view of the catheter delivery system of FIG. 1.

The cannula delivery housing 21 includes a main cylindrically-shaped housing 53 and a circular cap 55. The cap 55 has a hole therethrough at which the adaptor 51 is mounted. The cap 55 has a portion 57 that is of reduced diameter to fit into a large opening 59 of the cylindrically-shaped main housing 53 and forms a seal therewith. The portion of reduced size 57 has a slot 61 therein for receiving an O-ring 63 to form a seal with the interior wall of the cylindrically-shaped main housing 53. The cylindrically-shaped main housing 53 has a conically-shaped right end 65 (as viewed in FIGS. 1 and 4) converging at a mounting protrusion 67 having a passageway therethrough. The mounting protrusion 67 is adapted to pass through a hole in a lower portion 69 of a spring clamp 71. Tabs 73 of the spring clamp 71 cover the cap 55 and are held together by an O-ring 74 to hold the cap 55 on the main housing 53. A Touhy-Borst adaptor, for example, 75 attaches the mounting protrusion 67 to a catheterizing tube 11 which is inserted in a blood vessel. The right end of the Touhy-Borst adaptor 75 is shown in greater detail in FIG. 3. In this respect, a sealing clamp thereof includes a resilient washer 77, a rigid plastic washer 79, and a cap 81. The cap 81 has internal threads to engage external threads of a main portion 83 of the adaptor 75 to urge the rigid plastic washer 79 against the resilient washer 77 and thereby clamp the resilient washer 77 on the catheterizing tube 11.

In operation, a main artery is punctured and the catheterizing tube 11 inserted therein. A miniature balloon catheter, including a relatively long cannula 13 is extended through the spool valve 25 of the cannula-control fitting 14 and the wing screw 17 is tightened to clamp the cannula-control fitting 14 to the cannula 13 near the distal end thereof. The cannula delivery housing 21 must normally be threaded onto the cannula 13 in a disassembled state with the O-ring 74 being threaded onto the cannula first, the cap 55 second, the main housing 53 third, and the spring clamp 71 fourth. The cannula is pulled all the way through these members. The mounting hub 49 of the spool 25 is inserted into the adaptor 51 and screwed tightly therein by means of gripping protrusions 85.

Figures 2, 4:
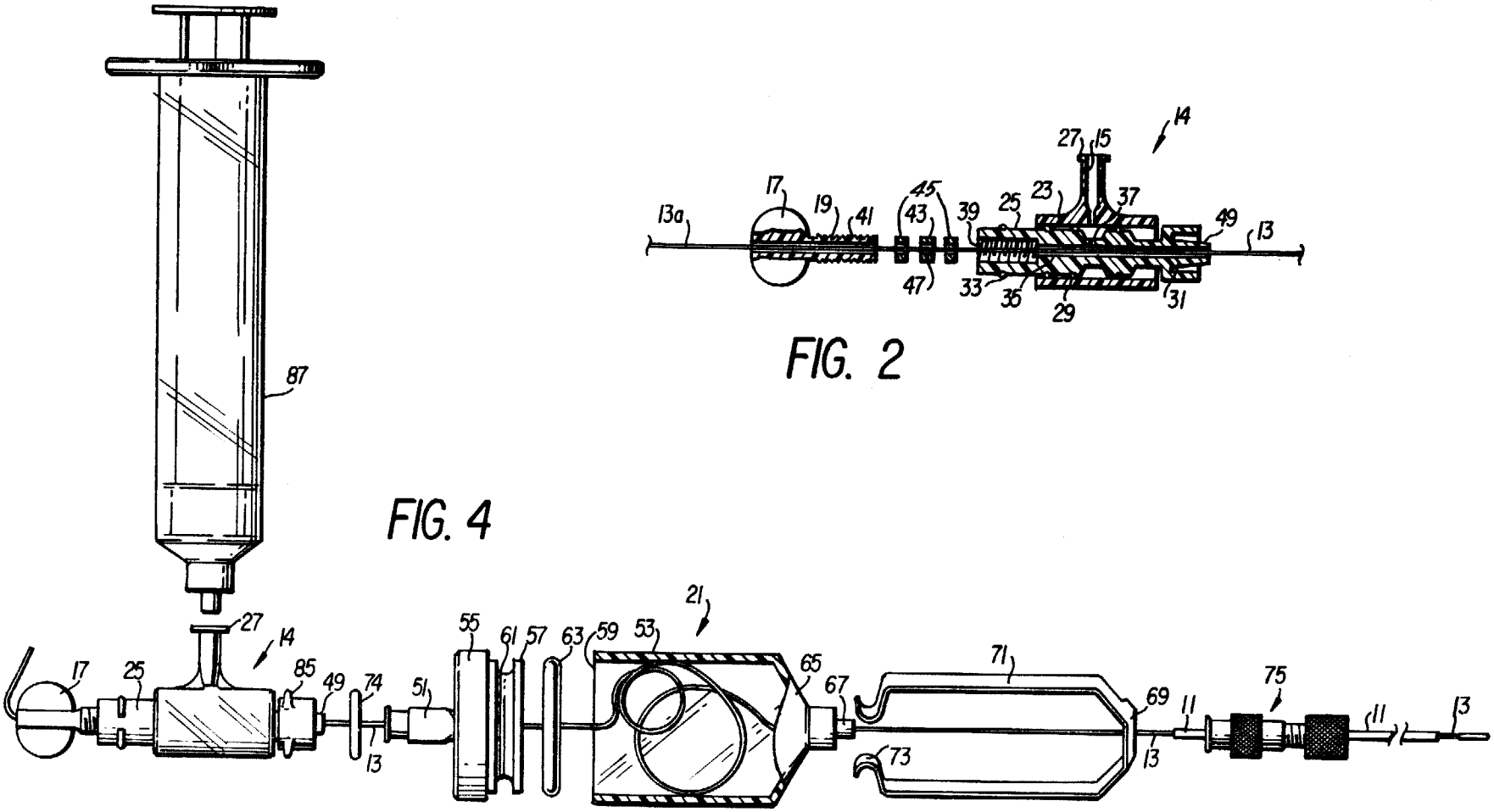
FIG. 2 is a sectional, partially exploded view of the cannula-control fitting of FIG. 1.

A syringe, or other pressurized fluid source, 87 is mounted on the coupling member 27 of the cannula-control fitting 14 and the sleeve 23 is placed in the position shown in FIG. 2, with its opening 15 communicating with the interior 35 of the spool 25. Syringe 87 is filled with a propelling fluid, such as a heparanized flush solution. This solution is forced by the syringe 87 first into the interior 35 of the spool 25 and from there into the cavity of the cannula delivery housing 21 to fill this up. The cannula 13 is then forced, by hand, back through the mounting protrusion 67 to be gathered in the cavity of the cannula delivery housing 21. The fluid in the cannula delivery housing 21 makes this procedure easier.

Once the cannula 13 is almost fully gathered in the cannula delivery housing 21, the balloon attachment, at the distal end of the cannula 13 is inserted into the proximal end of the catheterizing tube 11 and the mounting protrusion 67 is mounted onto the Touhy-Borst adaptor 75. The proximal end of the cannula is filled with radiopaque contrast media to visualize the cannula on a fluroscope. Now fluid is applied under pressure from the syringe 87 to drive the catheter 13 into the blood vessel through the catheterizing tube 11 until the cannula 13 that is gathered in the cannula delivery housing 21 is exhausted. At this point, the doctor loosens the wing screw 17 and thereafter manipulates the cannula 13 in the blood vessel by gripping the proximal end 13a of the cannula.

It should be understood by those skilled in the art that the catheter delivery system of this invention allows positive fluid propelling of long cannula-type catheters while also allowing doctors the flexibility of selectively manually manipulating such catheters where necessary or desired and significantly increases the *safety and* speed of cannula delivery.

Although this invention has been described with reference to a preferred embodiment, it should be understood by those skilled in the art that various modifications exist thereto within the scope of the invention. For example, the main housing could be filled with a fluid prior to putting its cap 55 on. Also, the cannula-control fitting 14 does not have to be a valve as is disclosed herein but can be merely a hollow housing having three openings therein, with one opening thereof including a sealing clamp for clamping onto a cannula passing therethrough.

I claim:

1. A catheter delivery system for delivering an elongated miniature cannula-type catheter to a body of a mammal and controlling the movement of the catheter tip in the mammal's body, the system comprising:

a miniature cannula-type catheter having a proximal end and a distal end;

a hollow cannula-control fitting having three openings therein, said cannula-control fitting including a coupling means for coupling a fluid source to the interior of said cannula-control fitting at a first opening, said second and third openings being positioned in substantial alignment to allow said cannula-type catheter to extend through said second and third openings, said proximal end extending out of said second opening and said distal end extending out of said third opening, said cannula-control fitting further including a clamping seal at said second opening for selectively clamping said cannula-control fitting to said cannula to create a seal at said second opening and for releasing said cannula-type catheter to allow longitudinal movement of said cannula through said second and third openings; and, a hollow cannula delivery housing defining a relatively large cavity for receiving gathered portions of said cannula-type catheter therein, said cannula delivery housing having an inlet opening and an outlet opening positioned on opposing sides of the cavity, said cannula delivery housing including a first attaching means at said inlet opening attaching said cannula delivery housing to said cannula-control fitting at said third opening thereof to bring the interior of the cannula-control fitting into communication with the cavity of said delivery housing and to allow said cannula-type catheter to extend from the third opening of said cannula-control fitting into said cannula delivery housing, said cannula delivery housing further including a tubular means at said outlet opening for attaching said cannula delivery housing to a mammal's blood vessel to communicate the cavity with said blood vessel and thereby allow said cannula-type catheter to extend through said outlet opening of said cannula delivery housing into said mammal's body.

2. A catheter delivery system as in claim 1 wherein said cannula-control fitting is a spool valve and includes a hollow sleeve having a hollow spool movable therein, said sleeve defining said first opening into the interior of said sleeve and said hollow spool defining said second and third openings, said spool having a passageway extending from the external surface thereof into the interior thereof, said sleeve being slidable along said spool to bring said first opening into communication with said passageway, said first attaching means of said cannula delivery housing attaching said cannula delivery housing to said spool at said third opening.

3. A catheter delivery system as in claim 2 wherein said clamping seal is mounted on said spool at said second opening thereof, said clamping seal comprising an externally threaded screw engaging internal threads of said spool, said clamping seal further including a resilient washer positioned between said screw and said spool to be squeezed, and thereby laterally extended onto said cannula-type catheter by said screw.

4. A catheter delivery system as in claim 2 wherein said cannula delivery housing includes a main hollow housing having a large opening at one end thereof and a small opening at the other end thereof and a selectively removable cap for engaging said main hollow housing to cover said large opening, said cap defining said inlet opening and said attaching means at said inlet opening.

5. A catheter delivery system as in claim 4 wherein said cap and said main housing are cylindrical in shape and said cap includes a smaller diameter portion which fits into the large opening of said main housing for forming a seal therewith.

6. A catheter delivery system as in claim 5 wherein is further included a metallic clamp extending about said main housing and said cap for holding said cap in engagement with said main housing said clamp including a resilient O-ring for holding said clamp together.

7. A catheter delivery system as in claim 4 wherein said main housing and said cap have circular cross-sections and the outlet end of said main housing has a conical shape merging toward said outlet opening.

8. A catheter delivery system as in claim 1 wherein said cannula delivery housing includes a main hollow housing having a large opening at one end thereof and a small opening at the other end thereof and a selectively removable cap for engaging said main hollow housing to cover said large opening, said cap defining said inlet opening and said attaching means at said inlet opening.

9. A catheter delivery system as in claim 8 wherein said cap and said main housing are cylindrical in shape and said cap includes a smaller diameter portion which fits into the large opening of said main housing for forming a seal therewith.

10. A catheter delivery system as in claim 9 wherein is further included a metallic clamp extending about said main housing and said cap for holding said cap in engagement with said main housing said clamp including a resilient O-ring for holding said clamp together.

11. A catheter delivery system as in claim 8 wherein said main housing and said cap have circular cross-sections and the outlet end of said main housing has a conical shape merging toward said outlet opening.

12. A catheter delivery system as in claim 1 wherein said cannula delivery housing comprises two parts which are held together in a sealed relationship to form said cavity by a selectively releasable clamp which contacts both parts.

13. A catheter delivery system as in claim 12 wherein said clamp encloses said cannula delivery housing, said selectively releasable clamp including a selectively adjustable means for reducing its size to thereby clamp said two parts together.

14. A catheter delivery system for delivering a large cannula-type catheter to a body of a mammal and controlling the movement of the catheter tip in the mammal's body, the system comprising:

a hollow cannula-control fitting, having three openings therein, said cannula-control fitting including a coupling means for coupling a fluid source to the interior of said cannula-control fitting at a first opening, said second and third openings being positioned and oriented to one another to allow said cannula to extend through the interior of said cannula-control fitting and to extend out of said cannula-control fitting at said second and third openings, said cannula-control fitting further including a clamping seal at said second opening for selectively clamping said cannula-control fitting to said cannula to create a seal at said second opening and for releasing said cannula to allow longitudinal movement of said cannula through said second openings; and, a hollow cannula delivery housing defining a relatively large cavity for receiving gathered portions of said cannula therein, said cannula delivery housing having an inlet opening and an outlet opening positioned on opposing sides of the cavity, said cannula delivery housing including a first attaching means at said inlet opening for attaching said cannula delivery housing to said cannula-control fitting at said third opening thereof to bring the interior of the cannula-control fitting into communication with the cavity of said delivery housing and to allow said cannula to extend from the third opening of said cannula-control fitting into said cannula delivery housing, said cannula delivery housing further including a second attaching means at said outlet opening for attaching said cannula delivery housing to a mammal's body to allow said cannula and its attached catheter to extend through said outlet opening of said cannula delivery housing into said mammal's body;

wherein said cannula delivery housing includes a main hollow housing having a large opening at one end thereof and a small opening at the other end thereof and a cap for engaging said main hollow housing to cover said large opening, said cap defining said inlet opening and said attaching means at said inlet opening, and wherein is further included a metallic clamp extending about said main housing and said cap for selectively holding said cap in engagement with said main housing said clamp including a resilient O-ring for holding said clamp together.

15. A method of delivering a long cannula catheter having proximal and distal ends comprising the steps of:

engaging the cannula catheter at a location intermediate its ends, but near its proximal end, with a cannula-control fitting having three openings therein, the cannula catheter extending through the second and third of these openings, said second and third openings being in substantial alignment;

clamping the cannula-control fitting to said cannula catheter at said second opening to form a seal therebetween;

bringing an inlet opening of an enlarged, hollow cannula delivery housing into communication with said third opening of said hollow-control fitting;

gathering most of the cannula catheter at its distal end in said enlarged hollow cannula delivery housing while leaving the distal tip of said cannula catheter extending out of said hollow cannula delivery housing at an outlet opening thereof;

inserting the distal tip of said cannula catheter into the body of a mammal and bringing said outlet opening of said hollow cannula delivery housing into communication with the body of a mammal;

applying liquid at the first opening into said cannula-control fitting to pass through said cannula-control fitting into said cannula delivery housing and drive said gathered cannula from said hollow cannula delivery housing into the mammal's body; and, unclamping the cannula-control fitting from said cannula catheter and manually manipulating the proximal end of said cannula catheter to manually manipulate the position of said cannula catheter in said mammal's body.

*16. A catheter delivery system for delivering an elongated miniature cannula-type catheter to a body of a mammal and controlling the movement of the catheter tip in the mammal's body, the system comprising:*

*a miniature cannula-type catheter having a proximal end and a distal end;*

*said catheter delivery system further comprising a conduit system including:*

*a hollow cannula delivery housing defining a relatively large cavity for receiving gathered portions of said cannula-type catheter therein, said cannula delivery housing having an inlet opening and an outlet opening positioned on opposite sides of the cavity, said cannula delivery housing further including a tubular means at the outlet opening for attaching said cannula delivery housing to a mammal's blood vessel to communicate the cavity with said blood vessel and thereby allow said cannula-type catheter to extend through said outlet opening of said cannula delivery housing into said mammal's body;*

*a hollow cannula-control member mounted at said inlet opening, said hollow cannula-control member having first and second openings therein positioned to allow said cannula-type catheter to extend through said hollow cannula delivery housing and said hollow cannula control member, said hollow cannula control member and said hollow cannula delivery housing being attached to one another at their respective second and inlet openings, said cannula control member further including a clamping seal for selectively clamping said cannula control member to said cannula-type catheter to create a seal preventing fluid flow between said first and second openings about said cannula-type catheter and for releasing said cannula-type catheter to allow longitudinal movement of said cannula-type catheter through said first and second openings by means of a hand manipulation applied to said cannula-type catheter outside of said first opening; and*

*a coupling means for coupling a fluid source to the interior of said conduit system on the distal side of said clamping seal.*

*17. A catheter delivery system as in claim 16 wherein said coupling means is positioned on the proximal side of said hollow cannula delivery housing.*

*18. A method of delivering a long cannula catheter having proximal and distal ends comprising the steps of: extending the long cannula catheter through a conduit system, said conduit system comprising a hollow cannula delivery housing defining a relatively large cavity for receiving gathered portions of said cannula-type catheter therein having inlet and outlet openings positioned on opposite sides of the cavity and a hollow cannula-control member mounted at the inlet opening, said hollow cannula-control member having first and second openings therein to allow said cannula catheter to extend through said hollow cannula delivery housing and said hollow cannula control member, said hollow-cannula control member and said hollow cannula delivery housing being attached to one another at their respective second and inlet openings, said hollow-cannula control member further including a clamping seal;*

*clamping the clamping seal of said cannula-control member to the cannula catheter to form a seal with said cannula catheter for inhibiting fluid flow between said first and second openings about said cannula catheter;*

*gathering most of the cannula catheter in said enlarged, hollow cannula delivery housing while leaving the distal tip of the cannula catheter extending out of the hollow cannula delivery housing at the outlet opening thereof;*

*inserting the distal tip of the cannula catheter into the body of a mammal and bringing said outlet opening of said hollow cannula delivery housing into communication with the body of the mammal;*

*applying liquid into said conduit system to pass through said conduit system and thereby drive the distal tip of said cannula catheter into the mammal's body; and*

*unclamping the cannula-control member from the cannula catheter and manually manipulating the proximal end of said cannula catheter to manually manipulate the position of said cannula catheter in said mammal's body.*

* * * * *